US011771863B1

(12) United States Patent
Alshan et al.

(10) Patent No.: US 11,771,863 B1
(45) Date of Patent: Oct. 3, 2023

(54) INTERFACE FOR GUIDED MEDITATION BASED ON USER INTERACTIONS

(71) Applicant: AMAZON TECHNOLOGIES, INC., Seattle, WA (US)

(72) Inventors: Eli Alshan, Kfar-Saba (IL); Mark Kliger, Modi'in (IL); Ido Yerushalmy, Tel-Aviv (IL); Liza Potikha, Netanya (IL); Dotan Kaufman, Netanya (IL); Ianir Ideses, Raanana (IL); Eduard Oks, Redmond, WA (US); Noam Sorek, Herzliya (IL)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 792 days.

(21) Appl. No.: 16/710,211

(22) Filed: Dec. 11, 2019

(51) Int. Cl.
*G08B 21/04* (2006.01)
*A61M 21/02* (2006.01)
*G16H 10/60* (2018.01)
*G16H 50/30* (2018.01)
*G16H 20/00* (2018.01)
*G06Q 10/1093* (2023.01)
*G06V 40/20* (2022.01)
*G06V 40/16* (2022.01)
*A61M 21/00* (2006.01)

(52) U.S. Cl.
CPC ............ *A61M 21/02* (2013.01); *G06Q 10/1097* (2013.01); *G06V 40/176* (2022.01); *G06V 40/23* (2022.01); *G16H 10/60* (2018.01); *G16H 20/00* (2018.01); *G16H 50/30* (2018.01); *A61M 2021/0016* (2013.01); *A61M 2021/0022* (2013.01); *A61M 2021/0044* (2013.01); *A61M 2021/005* (2013.01); *A61M 2205/3306* (2013.01); *A61M 2205/3375* (2013.01); *A61M 2205/50* (2013.01); *A61M 2205/52* (2013.01); *A61M 2230/04* (2013.01); *A61M 2230/06* (2013.01); *A61M 2230/20* (2013.01); *A61M 2230/30* (2013.01); *A61M 2230/42* (2013.01); *A61M 2230/50* (2013.01); *A61M 2230/62* (2013.01); *A61M 2230/63* (2013.01)

(58) Field of Classification Search
USPC .. 340/539.12, 539.22, 539.25, 555, 566, 575, 340/636.11, 636.18, 691.2, 825.25, 5.52, 5.53, 340/5.83, 7.6
See application file for complete search history.

(56) References Cited

U.S. PATENT DOCUMENTS

10,424,183 B1 * 9/2019 Kahn et al. ............ G08B 21/24
11,529,096 B2 * 12/2022 Watanabe et al. ....... A61H 7/00
(Continued)

*Primary Examiner* — Daniel Previl
(74) *Attorney, Agent, or Firm* — Lindauer Law, PLLC (57) ABSTRACT

Systems for assisting a user in performance of a meditation activity or another type of activity are described. The systems receive user input and sensor data indicating physiological values associated with the user. These values are used to determine a recommended type of activity and a length of time for the activity. While the user performs the activity, sensors are used to measure physiological values, and an output that is provided to the user is selected based on the measured physiological values. The output may be selected to assist the user in reaching target physiological values, such as a slower respiration rate. After completion of the activity, additional physiological values are used to determine the effectiveness of the activity and the output that was provided. The effectiveness of the activity and the output may be used to determine future recommendations and future output.

20 Claims, 6 Drawing Sheets

(56) References Cited

U.S. PATENT DOCUMENTS

| | | | |
|---|---|---|---|
| 2014/0254902 A1* | 9/2014 | Sugawara et al. | G06V 40/11 |
| | | | 382/128 |
| 2016/0089059 A1* | 3/2016 | Hu | A61B 5/7207 |
| | | | 600/595 |
| 2016/0151603 A1* | 6/2016 | Shouldice et al. | A61B 5/4806 |
| | | | 600/26 |
| 2016/0270717 A1* | 9/2016 | Luna et al. | A61B 5/743 |
| 2019/0083030 A1* | 3/2019 | Thakur et al. | A61B 5/7275 |
| 2021/0022669 A1* | 1/2021 | Ting et al. | A61B 5/4809 |
| 2021/0052225 A1* | 2/2021 | Shetty et al. | A61B 5/082 |
| 2021/0117432 A1* | 4/2021 | Hofstetter et al. | G06F 16/24575 |

* cited by examiner

INTERFACE FOR GUIDED MEDITATION BASED ON USER INTERACTIONS

BACKGROUND

Certain types of activities, such as meditation, yoga, and so forth, may be more effective based on the physiological state of the individual performing the activity. For example, the positive effects associated with meditation may be more readily experienced if an individual is able to reduce their heart rate and respiratory rates to values associated with a relaxed state. However, applications executed by a user's device, as well as physical and virtual classes with instructors, typically rely upon scripted content that may proceed to other portions of a meditation activity before a user has reached a physiological state that is suitable to proceed with the activity.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

While implementations are described in this disclosure by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used in this disclosure are for organizational purposes only and are not meant to be used to limit the scope of the description or the claims. As used throughout this application, the word "may" is used in a permissive sense (i.e., meaning having the potential to) rather than the mandatory sense (i.e., meaning must). Similarly, the words "include", "including", and "includes" mean "including, but not limited to".

DETAILED DESCRIPTION

Various types of activities, such as meditation and yoga, may provide benefits such as improved focus and concentration, improved quantity and quality of sleep, reduced stress, and so forth. As such, some users may acquire and execute applications on various computing devices to assist the user in performing guided meditation or other types of activities. Typically, a guided meditation application will cause instructional prompts, music, and other types of sound to be output based on the length of time that has elapsed. For example, a meditation activity may be subdivided into particular phases or portions, with each portion of the activity lasting a preselected length of time before proceeding to the next portion. However, each user may respond differently to different types of content. For example, a particular user may readily reach a relaxed physiological state, exhibited by a reduced heart rate and respiratory rate, when certain content is output, while a different user may experience different results. Additionally, the effect of certain content on the particular user may vary depending on the personal circumstances affecting the user at the time that the activity is performed. In some cases, if a user's heart rate, respiratory rate, or other physiological values do not reach target values before proceeding to a subsequent portion of a meditation activity, the benefits experienced by the user may be suboptimal. Additionally, a user that lacks detailed knowledge regarding meditation or other similar activities may select a type of meditation or a length of time for a meditation activity that is not suitable for achieving the user's desired goals, or that may be less effective based on the user's physiological state.

Described in this disclosure are techniques for assisting a user in performing a guided meditation activity, or other types of activities that may be affected by or may affect the user's heart rate, respiratory rate, or other physiological values. When an activity is initiated, a first output may be provided to an output device associated with the user. The first output may include image data, video data, audio data, haptic data, olfactory data, or other types of data. For example, the first output may include instructional prompts regarding a stationary body position, a type of movement, a count of breaths to attempt to take within a certain length of time, a type of breathing to undertake, a body part or other topic on which to focus mentally, and so forth. As another example, the first output may include music or other types of sound that may affect the physiological state of the user or indicate certain actions to the user. For example, slower music may be provided to a user to indicate that the user's respiratory rate is above a selected value. The slower music may be intended to cause the user to focus on reducing the respiratory rate or to induce a relaxed state in which the user will naturally exhibit a lower respiratory rate.

As the user performs the activity, sensors that are worn by the user or positioned in an environment with the user may determine physiological values, such as the user's heart rate, respiratory rate, blood pressure, heart rate variability, oxygen saturation, temperature, blood perfusion index, and in some cases, physical characteristics of the user, such as a user's body position or weight. The blood perfusion index may include the ratio of pulsatile blood flow to nonpulsatile (or static) blood flow in peripheral tissue, measured during arterial inflow. The perfusion index may be calculated based on the amount of infrared light absorbed by a user's body at a monitoring site. Prior to beginning the activity, the user may be provided with an interface to consent or opt-in for determination of the physiological values using the sensors. Subsequent output that is presented to the user may be determined based at least in part on the physiological values. For example, if a user's respiratory rate has not decreased sufficiently to proceed to a subsequent portion of a meditation activity, the subsequent output may include an instruction to the user to focus on a reduced respiratory rate, music or sound that may cause the userto breathe more slowly, and so forth. As another example, when a user's respiratory rate, heart rate, and other physiological values reach target values that are sufficient to proceed to a subsequent portion of the activity, subsequent output may be provided immediately, in response to the physiological values. As a result, the output that is provided to the user may be customized to the current physiological values associated with the user, and changed as the physiological values change, which may increase the benefits of the meditation or other type of activity. In some implementations, the determined physiological values may be encrypted, anonymized, de-identified and so forth.

In some implementations, user input, data from sensors associated with a user, or both user input and sensor data may be used to provide a recommendation for a type of activity and a length of time for performance of the activity. For example, a user may provide input data indicating the user's age, weight, health conditions, or other physical characteristics, and may also provide permission for collection of physiological information using sensors. In some cases, the user may also input subjective characteristics such as whether the user is feeling stressed or fatigued, a perceived quality of the user's sleep, a number of hours the user slept the previous night, and so forth. In some implementations, the user may also indicate one or more goals for performance of the activity, such as improved focus and concentration, improved quantity or quality of sleep, reduced stress, and so forth. Additionally, data determined from sensors, such as a user's blood pressure, heart rate, respiration rate, and so forth may indicate stress or fatigue, or conversely, may indicate that the user is in a relaxed physiological state. In some implementations, data from a microphone may be used to determine an emotional state of the user based on characteristics of the user's speech. In other implementations data from a camera may be used to determine characteristics of the user based on the user's facial expression or body position. In still other implementations, calendar data associated with the user may indicate one or more available times for performance of an activity. As such, a recommendation may indicate a type of activity, a length of time for the activity, and in some cases, a particular time for performance of the activity, based on data input by the user and data determined using various sensors associated with the user.

After completion of the activity, additional data may be determined via user input or using one or more sensors. The user may be provided with an interface requesting permission for collection of the additional data. For example, a user may report an improved, diminished, or unchanged quality or quantity of sleep, increased or decreased focus and concentration, increased or decreased stress, and so forth. Additionally, physiological values determined from the sensors may indicate changes in the user's heart rate or other physiological values that may indicate that the user has become more relaxed, less relaxed, or that the user's physiological state has not changed. The effectiveness of different activities and different output presented to the user may be used to determine future output provided to the user and to other similar users. For example, one or more machine learning algorithms may be used to process input data and physiological values determined from users before, during, and after presentation of different output and performance of different activities.

As a result, a user may be provided with customized output based on physiological values determined for the user, which may facilitate selection of an activity that optimizes the possible benefits conferred to the user. Additionally, during performance of the activity, the output that is presented may be selected and changed as the user's physiological values change, further optimizing the benefit of the activity. Information determined after the activity has been performed may enable subsequent recommendations and subsequent output that is presented to be further customized to increase the benefit to the user.

Figure 1:
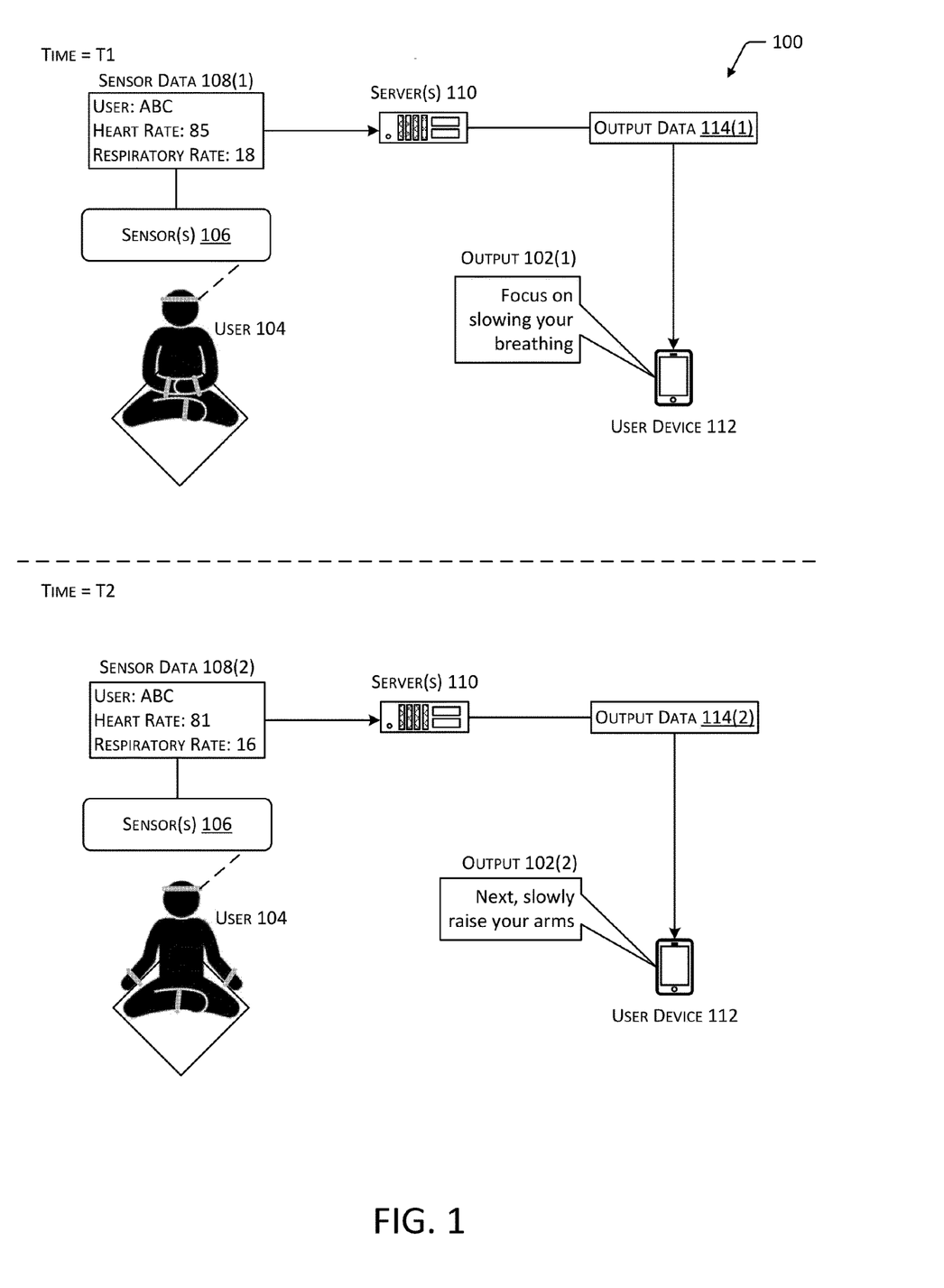
FIG. 1 depicts an implementation of a system for determining output to present to a user based on physiological values associated with the user.

FIG. 1 depicts an implementation of a system 100 for determining output 102 to present to a user 104 based on physiological values associated with the user 104. The output 102 may be associated with performance of a particular type of activity, such as a meditation activity. For example, the output 102 may include instructional prompts, such as prerecorded speech or simulated speech that is generated for presentation, or other types of sound, such as music. In other implementations, the output 102 may include images, video, haptic output, olfactory output, or other types of output. For example, output 102 may include music or sounds to facilitate performance of the activity.

As the user 104 performs the activity, one or more sensors 106 associated with the user 104, or the environment proximate to the user 104, may acquire sensor data 108(1). For example, sensors 106 may include devices that are worn or carried by the user 104. The sensors 106 may generate sensor data 108(1) indicative of various physiological values associated with the user 104, such as a blood pressure, cardiac pulse (e.g., heart rate), temperature, blood perfusion index, respiration rate, oxygen saturation, heart rate variability, and so forth. Continuing the example, a sensor 106 may include a photoplethysmograph (PPG), which may be used to determine a respiratory rate and other physiological values of the user 104. For example, a PPG may use optical components to detect blood volume changes in the microvascular bed of tissue, such as by illuminating the skin of the user 104 and measuring changes in light absorption. Changes in light absorption may be caused by the perfusion of blood throughout the skin. In some cases, a PPG may also measure a pressure pulse due to the distension of arteries caused by each cardiac cycle. The change in volume caused by the pressure pulse may be detected by illuminating the skin with light, such as light from a light emitting diode (LED), and measuring the amount of light that reaches a photodiode. A PPG may also monitor breathing, hypovolemia, and various circulatory conditions. In some cases, a PPG may be used to measure blood pressure and may operate in conjunction with a temperature sensor for measuring a temperature of the user 104. Worn or held sensors 106 may also be used to determine the position of one or more body parts of the user 104, movement of the user 104, and so forth. Worn or held sensors 106, such as galvanic skin response (GSR) sensors, may also be used to measure other physiological values determined based on contact with or proximity to the user 104, such as sweat gland activity. For example a GSR sensor may detect changes in conductivity or other electrical activity resulting from changes in sweat gland activity of a user 104. As another example, the sensors 106 may include one or more cameras. Continuing the example, a camera may generate sensor data 108(1) indicative of a position of one or more body parts of the user 104, such as image data indicating a posture of the user 104, whether the eyes of the user 104 are open or closed, or a facial expression of the user 104. For example, image data from a camera may be used to determine a position of the user 104, which may be compared to a reference position indicative of a desired posture or other body position. Image data from a camera may also be used to determine dimensions of one or more body parts of the user 104, a weight or other physical characteristics of the user 104, and so forth. In some cases, a camera may be used to visualize veins or other internal structures of the body for determining physiological values, such as heart rate or blood pressure. Additionally, a camera may be used to visualize movement of a chest or stomach of the user 104, such as to determine a respiratory rate or type of breathing undertaken by the user 104, a direction of a gaze of the user 104, movement of the eyes of the user 104 when closed, and so forth. Other sensors 106 associated with the user 104 or environment may also be used. For example, a pressure sensor or position sensor may be used to determine the presence of the user 104 at a particular location, a weight of the user 104, and so forth. Continuing the example, FIG. 1 depicts the user 104 positioned on a sensor 106 having the form factor of a floor mat.

The sensor data 108(1) may be processed to determine one or more physiological values associated with the user 104. For example, FIG. 1 depicts the sensor data 108(1) including an identifier indicative of the user 104 and values indicating a heart rate and a respiratory rate of the user 104. The sensor data 108(1) may be provided to one or more servers 110 via one or more networks. In other implementations, the sensor data 108(1) may be received by one or more computing devices in an environment with the user 104, and use of a separate server 110 may be omitted. For example, a user device 112 that is used to present output 102 to the user 104 may also receive sensor data 108(1) and determine subsequent output 102 for presentation based on the sensor data 108(1). While FIG. 1 depicts an example user device 112 as a smartphone, the user device 112 may include any type of computing device including, without limitation, servers, personal computers, wearable computing devices, portable computing devices, automotive computing devices, smart televisions, networked speaker devices, and so forth. Additionally, multiple computing devices may be used to perform the functions described with regard to the user device 112. The server(s) 110 may include any number and any type of computing device including, without limitation, the types of computing devices described with regard to the user device 112. In other implementations, one or more sensors 106 may perform the functions described with regard to the server(s) 110 or user device 112. For example, a wearable computing device may be used to acquire sensor data 108, determine an output 102 based on the sensor data 108, and present the output 102.

The server(s) 110 or other computing device(s) may determine output data 114(1) based on the physiological values represented by the sensor data 108(1), then provide the output data 114(1) to the user device 112 for presentation of output 102(1) based on the output data 114(1). In some implementations, the server(s) 110 may access activity data that associates particular output data 114(1) with corresponding physiological values. For example, the sensor data 108(1) shown in FIG. 1 indicates a respiratory rate of 18. In response to this respiratory rate exceeding a threshold value or deviating from a threshold range, particular output data 114(1) that corresponds to this determination may be provided to the user device 112. The output data 114(1) may be used to present an output 102(1) intended to cause the user 104 to modify their respiratory rate. For example, the output 102(1) may include an instruction to focus on slower breathing. As other examples, the output 102(1) may include music or sounds intended to induce relaxation or otherwise cause a slower respiratory rate. As such, the output 102(1) that is presented to the user 104 may vary depending on the sensor data 108(1) that is acquired by the sensors 106.

At a second time T2 subsequent to the first time T1, second sensor data 108(2) may be acquired by the sensor(s) 106. For example, in response to the output 102(1), the user 104 may perform the activity in a manner that causes the physiological values determined at the first time T1 to change. Continuing the example, FIG. 1 depicts the sensor data 108(2) acquired at the second time T2 indicating a slower heart rate and respiratory rate than the sensor data 108(1) acquired at the first time T1. In response to the second sensor data 108(2), the server(s) 110 may determine output data 114(2) that corresponds to the physiological values of the second sensor data 108(2). For example, FIG. 1 depicts the server(s) 110 providing second output data 114(2) to the user device 112, which may present second output 102(2). Continuing the example, in response to a respiratory rate that is less than a threshold value, the output 102(2) may proceed to a subsequent portion of a meditation activity.

Figure 2:
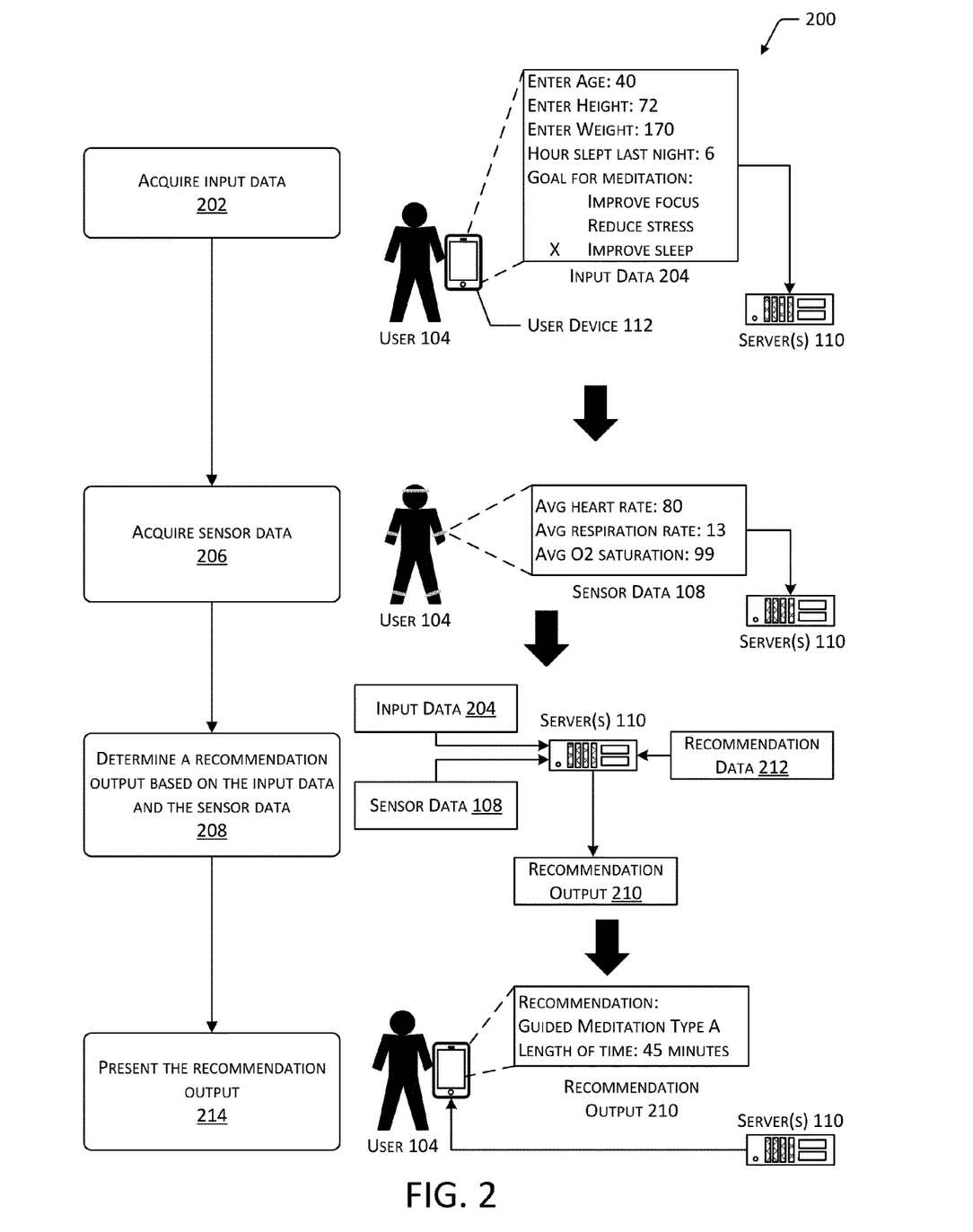
FIG. 2 depicts a scenario illustrating a method for generating a recommendation for a type of activity and length of time for the activity based on input data and sensor data.

FIG. 2 depicts a scenario 200 illustrating a method for generating a recommendation for a type of activity and length of time for the activity based on input data and sensor data 108. At 202, input data 204 may be acquired from the user 104. For example, the user device 112 may include one or more input devices, such as a touchscreen, keyboard, microphone, and so forth, and may present one or more user interfaces for soliciting user input. For example, FIG. 2 depicts the input data 204 including an age, height, and weight of the user 104, as well as an indication of a number of hours that the user 104 slept and one or more selectable goals of the user 104 associated with performance of the activity. In some implementations, the input data 204 may also include an indication of one or more health conditions or physiological values. For example, a user 104 may provide user input indicating a blood pressure, temperature, heart rate, respiration rate, and so forth. User interfaces may also be used to request permission from the user 104 for use of the input data 204, collection of sensor data 108, and so forth, such as by including a form or one or more controls enabling the user 104 to opt-in for collection and use of data. The input data 204 may be used to determine a recommendation to present regarding a type or length of time for an activity. For example, input data 204 may indicate various characteristics of the user 104. Continuing the example, in response to input data 204 indicating that the user 104 slept a number of hours less than a threshold value or indicating a goal to improve a quantity or quality of sleep, the server(s) 110 or another computing device may determine a recommendation for an activity intended to improve the quantity or quality of sleep may be presented.

At 206, sensor data 108 may be acquired from one or more sensors 106 associated with the user 104. As described with regard to FIG. 1, sensors 106 may include held or wearable devices, one or more cameras, microphones, position or pressure sensors, and so forth. For example, one or more wearable sensors 106 may acquire sensor data 108 indicative of a heart rate, respiration rate, and oxygen saturation value associated with the user 104. In some implementations, the sensor data 108 may be encrypted, anonymized, de-identified, and so forth prior to providing the sensor data 108 to the server(s) 110 or another computing device. The sensor data 108 may be used to determine a recommendation to present regarding a type or length of time for an activity. For example, sensor data 108 indicating a heart rate or respiration rate above a threshold value may indicate stress or fatigue associated with the user 104. In such a case, the server(s) 110 or another computing device may determine a recommendation for an activity to reduce stress.

In some implementations, the first sensor data 108(1) may include data acquired using a camera. For example, image data indicative of a facial expression of a user 104 may be used to determine an emotional or physiological state of the user 104. Continuing the example, a particular facial expression or other facial characteristics may indicate tension, fatigue or lack of sleep, and so forth. In such a case, the server(s) 110 or another computing device may determine a recommendation for an activity to reduce stress, fatigue, or other physiological states determined based on the facial expression of the user 104. As another example, sensor data 108(1) acquired using a camera may indicate a body position of the user 104, such as a posture, movement of the user, and so forth. Continuing the example, the posture or other body position of the user 104, the rate at which the user 104 moves, or the manner in which the user 104 moves may indicate stress, fatigue, or other physiological states. In such a case, the server(s) 110 or another computing device may determine a recommendation for an activity to modify the physiological state determined based on the body position or movement of the user 104.

In some implementations, the first sensor data 108(1) may include data acquired using a microphone, such as speech of the user 104 or other non-speech utterances made by the user 104. Based on characteristics of the speech, such as a tone or tempo of voice or the particular words that are spoken, an emotional or physiological state of the user 104 may be determined. Similarly, non-speech utterances may indicate emotional or physiological states. In such a case, the server(s) 110 or another computing device may determine a recommendation for an activity to modify the physiological state determined based on the or utterances of the user 104.

At 208, a recommendation output 210 may be determined based on the input data 204 and the sensor data 108. For example, the server(s) 110 or another computing device may determine correspondence between one or more of the input data 204 or sensor data 108 and recommendation data 212. The recommendation data 212 may associate particular physiological values or characteristics of the user 104 with corresponding recommendation outputs 210. Based on the recommendation data 212, the server(s) 110 may determine a particular recommendation output 210 that corresponds to one or more of the characteristics determined from the input data 204 or the physiological values determined from the sensor data 108.

At 214, the recommendation output 210 may be provided to the user device 112 for presentation. For example, FIG. 2 depicts the recommendation output 210 indicating a type of activity and length of time for the type of activity that corresponds to the characteristics of the user 104 determined from the input data 204 and the physiological values of the user 104 determined from the sensor data 108.

Figure 3:
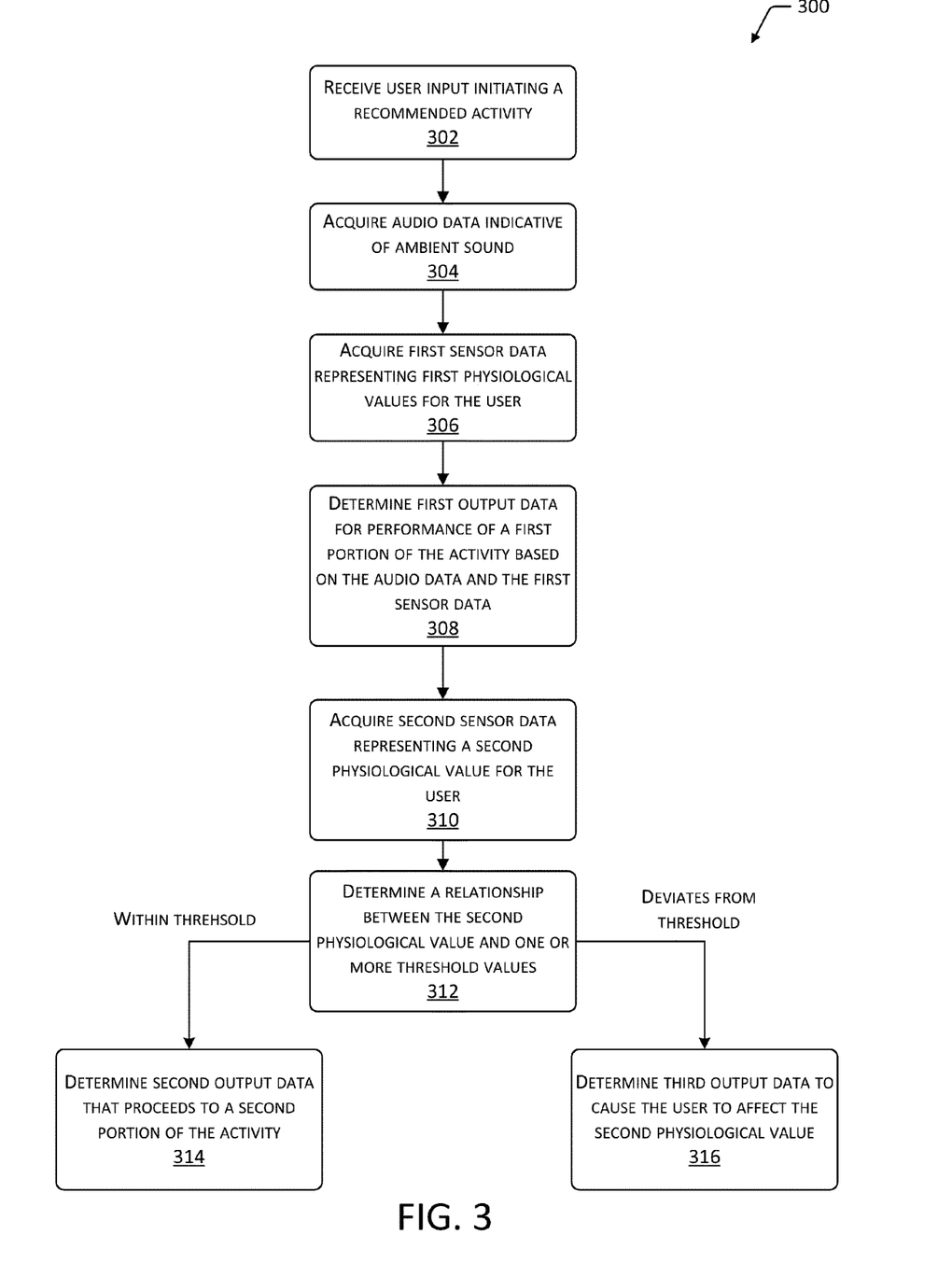
FIG. 3 is a flow diagram illustrating a method for determining output data based on sensor data associated with a user.

FIG. 3 is a flow diagram 300 illustrating a method for determining output data 114 based on sensor data 108 associated with a user 104. At 302, user input initiating a recommended activity may be received. As described with regard to FIG. 2, a recommendation output 210 may be presented that indicates one or more of a type of activity or a length of time for performance of an activity. In some implementations, the recommendation output 210 may also include an indication of one or more times for performance of the activity. For example, calendar data associated with the user 104 may be determined, which may indicate one or more times that are available for performance of the activity. Continuing the example, the calendar data may indicate times associated with particular tasks, and in some cases, times that are not associated with tasks and may therefore be available for performance of the activity. Based on the calendar data and the length of time associated with the activity, particular available times having a length sufficient for performance of the activity may be included in the recommendation output 210. In some implementations, a recommendation output 210 may include multiple times, multiple lengths of time, or multiple possible activities, and the user input may select a particular recommended activity. In other implementations, the recommendation output 210 may include a single activity, and the user input may accept the recommendation output 210. For example, in response to selection of the single activity, an indication of the activity may be added to the calendar data associated with the user 104.

At 304, audio data indicative of ambient sound may be determined. For example, one or more of the sensors 106 may include a microphone that acquires audio data representing sound in the environment proximate to the user 104, or in some cases, speech by the user 104 or other individuals. Audio data may be used to determine subsequent output 102 presented to the user 104. For example, if the volume or type of sound in an environment hinders or prevents performance of an activity, output 102 that is presented may include a recommendation to move to a different location, an indication of the unfavorable sound, and so forth. In other implementations, the type or volume of the output 102 that is presented may be determined based in part on the audio data. For example, if a volume of ambient sound in an environment is high, output 102 having a higher volume or a type that is audible within the environment may be presented. Ambient sound may include speech of the user 104 or other individuals in the environment, or other sounds that occur in the environment. In some implementations, the determined audio data may include unintelligible samples to conserve computational resources and improve privacy and security. For example, audio data may be analyzed at a particular sampling rate, such as every tenth frame, which may be used to determine a volume of noise in an environment without reconstructing speech that occurred in the environment. In other implementations, acquisition of audio data may be omitted and output 102 may be provided based on other data, such as sensor data 108.

At 306, first sensor data 108(1) representing first physiological values for the user 104 may be acquired. For example, sensors 106 worn or carried by the user 104 or within the environment proximate to the user 104 may determine physiological values associated with the user 104. The physiological values determined from the sensor data 108(1) may be used to determine output 102 that is presented to the user 104. For example, if a physiological value deviates from a threshold value, subsequent output 102 that is presented may include an instruction to perform the activity in a manner that may cause the physiological value to change. If the physiological value corresponds to a threshold value, subsequent output 102 may progress to the next portion of the activity.

In some implementations, prior to acquiring the first sensor data 108(1) representing the first physiological values, sensor data 108 may be acquired to determine that motion of the user 104 is less than a threshold value. For example, movement of the user 104 may prevent or decrease the accuracy associated with measurement of particular physiological values, such as a respiratory rate or a resting heart rate. Determining that the user 104 is not moving or that the motion of the user is less than a threshold prior to acquiring the first sensor data 108(1) may improve the accuracy of the determined physiological values. Determination of motion of the user 104 may include use of one or more cameras, such as by determining changes in the position of the body of the user 104 over time. In other implementations, determination of motion may include use of one or more of accelerometers, gyroscopes, motion or locations sensors, position sensors, and so forth. The threshold value for the motion of the user 104 may include a rate of movement for any part of the body of the user 104 or for only particular parts of the body. For example, if a heart rate sensor is associated with a wearable device on the left wrist of the user 104, the threshold value may be associated with movement of the left arm, while motion of other body parts of the user 104 may be disregarded. In some cases, motion of the user 104 may be determined using the same sensor(s) 106 that are used to acquire physiological values. For example, if a physiological value determined using a sensor 106 includes a large amount of variation, noise, and so forth, this may indicate motion of the user 104.

At 308, first output data 114(1) for performance of a first portion of the activity may be determined based on the audio data and the first sensor data 108(1). For example, the server(s) 110 or another computing device may determine correspondence between the audio data and first sensor data 108(1) and activity data. The activity data may associate particular output data 114 with corresponding physiological values or characteristics of the environment indicated by the audio data.

At 310, second sensor data 108(2) representing a second physiological value for the user 104 may be determined. For example, during performance of the activity by the user 104, such as while output 102 based on the first output data 114(1) is being presented, sensor data 108(2) may be acquired. The sensor data 108(2) may indicate physiological values associated with the user 104 during performance of the activity. For example, performance of the activity may affect a heart rate, respiration rate, blood pressure, or other physiological values, and as such, the physiological values indicated by the second sensor data 108(2) may differ from those indicated by the first sensor data 108(1) acquired at 306. The physiological values determined from the second sensor data 108(2) may be used to determine subsequent output 102 that is presented. For example, if a heart rate, respiration rate, or blood pressure of a user 104 exceed a threshold value during a meditation activity, this may indicate that the user 104 has not reached a sufficiently relaxed physiological state to proceed to a second portion of the meditation activity. In such a case, the subsequent output 102 that is presented may instruct the user 104 to continue performing the activity in a manner that may cause the physiological value to decrease. In cases where the determined physiological value(s) are within a threshold range, the subsequent output 102 may be associated with performance of a subsequent portion of the activity.

At 312, a relationship between the second physiological value of the second sensor data 108(2) and one or more threshold values may be determined. For example, a first threshold value for a respiration rate may be a minimum threshold value and a second threshold value for the respiration rate may be a maximum threshold value. If the physiological value determined from the second sensor data 108(2) is not between the first threshold value and second threshold value, the method of FIG. 3 may proceed to 316. If the physiological value is within the threshold range, the method may proceed to 314.

In some implementations, one or more threshold values may be determined based in part on previous data acquired from the user 104. For example, sensor data 108 acquired during performance of previous activities by the user 104, or during a previous time period independent of performance of an activity, may be used to determine an average heart rate, an average respiratory rate, or other physiological values. The threshold values may be determined based on the historical data acquired from the user 104. Historical data may include one or more historical values for a particular physiological characteristic, such as one or more previous values determined for a heart rate of the user 104. For example, a threshold heart rate indicative of a relaxed physiological state may include a value that is within a selected range, such as five percent, of an average resting heart rate for the user 104 that is determined based on historical values. In some implementations, historical values may include values obtained during a particular time period. For example, historical values acquired during performance of a previous activity by a user 104 may be used to determine one or more threshold values for future performance of the same activity by the user 104. In other cases, input data 204 that is previously acquired from the user 104 may be used to determine one or more threshold values. For example, one or more threshold values may be based on a weight, height, age, or other data input by the user 104. Continuing the example, a threshold heart rate or respiration rate may be calculated based on the age or weight of a user 104.

At 314, in response to a physiological value that corresponds to the one or more threshold values, second output data 114(2) that proceeds to a second portion of the activity may be determined. For example, if the physiological values associated with the user 104 are within target threshold ranges, this may indicate that the user 104 has achieved a desired physiological state, in response to which output 102 associated with a subsequent portion of the activity may be presented.

At 316, in response to a physiological value that deviates from the one or more threshold values, third output data 114(3) intended to cause the user 104 to affect the physiological value may be determined. For example, if a physiological value associated with the user 104 deviates from a target threshold range, output 102 that instructs the user 104 to perform in a manner that may cause the physiological value to increase or decrease, to reach the threshold range, may be presented.

Figure 4:
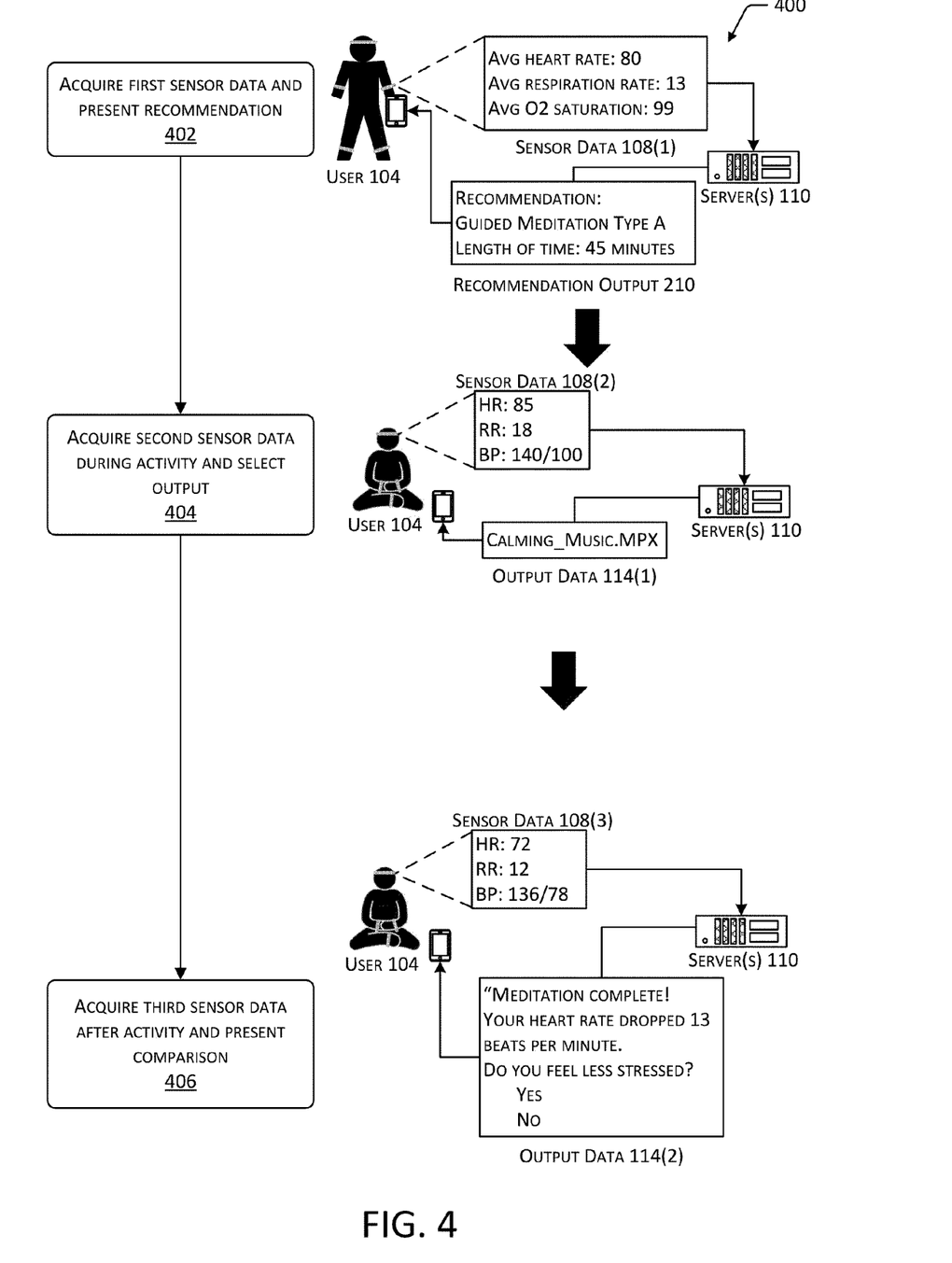
FIG. 4 depicts a scenario illustrating a method for determining the effect of an activity on one or more physiological values and presenting output indicative of the effect.

FIG. 4 depicts a scenario 400 illustrating a method for determining the effect of an activity on one or more physiological values and presenting output 102 indicative of the effect. At 402, first sensor data 108(1) may be acquired from one or more sensors 106 associated with a user 104 and a recommendation based on the sensor data 108(1) may be presented. As described with regard to FIGS. 1-3, sensor data 108(1) may indicate one or more physiological values associated with the user 104. In some implementations, the first sensor data 108(1) may include multiple values for a particular physiological characteristic and may be acquired over a period of time. For example, FIG. 4 depicts the first sensor data 108(1) indicating an average heart rate, an average respiration rate, and an average oxygen saturation that may be determined based on multiple values acquired over time. In some implementations, one or more sensors 106 associated with the user 104 may determine average physiological values or other types of values based on the physiological values. In other implementations, the server(s) 110 or another computing device may determine average values, or other types of values, based on sensor data 108 received from the sensors 106. Based on one or more of the physiological values indicated by the sensor data 108(1), the server(s) 110 or another computing device may determine a recommendation output 210. For example, one or more of the physiological values may indicate stress or fatigue, and the recommendation output 210 may indicate a type of activity or length of time for the activity that is intended to reduce stress or fatigue. As another example, a physiological value may indicate a blood pressure greater than a threshold value, and the recommendation output 210 may indicate a type of activity or length of time for the activity that is intended to reduce the blood pressure of the user 104.

At 404, second sensor data 108(2) may be acquired during performance of the activity by the user 104, and output 102 may be selected for presentation based on the sensor data 108(2). As described with regard to FIGS. 1 and 3, during performance of an activity, one or more sensors 106 worn or carried by the user 104, or in an environment with the user 104, may acquire sensor data 108(2) indicative of one or more physiological values or other characteristics of the user 104. For example, FIG. 4 depicts the sensor data 108(2) indicating values for a heart rate, respiration rate, and blood pressure of the user 104. In other implementations, sensor data 108(2) may include video data or image data acquired using a camera, such as data that indicates a posture or other body position of the user 104, a facial expression of the user 104, and so forth. For example, image data acquired using a camera may be used to determine a body position of a user 104, which may be compared to a reference position that indicates a desired posture or other body position. Continuing the example, if the body position of the user 104 deviates from the reference position by at least a threshold value, output 102 that provides instruction regarding the body position of the user 104 may be presented. In still other implementations, sensor data 108(2) may include audio data, such as speech or other sound produced by the user 104 or produced by other sources in the environment proximate to the user 104. Based on the sensor data 108(2) that is determined, output data 114(1) that corresponds to or is indicative of one or more of the physiological values indicated in the sensor data 108(2) may be provided to a user device 112 or another computing device for presentation of an output 102. For example, in response to physiological values indicating stress or tension, such as a heart rate, respiration rate, or blood pressure that is greater than a threshold value, the output data 114(1) may include audio data, such as music or other sound intended to facilitate relaxation of the user 104 and cause one or more of the determined physiological values to decrease. In other implementations, the output data 114(1) may be used to output prerecorded or synthesized speech, such as verbal prompts or instructions to cause changes in the physiological value(s). In still other implementations, the output data 114(1) may cause the output of images, video, a haptic output, an olfactory output, and so forth.

At 406, third sensor data 108(3) may be acquired after performance of the activity. The third sensor data 108(3) may be used to present a comparison or other type of result to the user 104. For example, FIG. 4 depicts the third sensor data 108(3) indicating a heart rate, respiration rate, and blood pressure that are less than those indicated by the second sensor data 108(2). Based on the second sensor data 108(2) and the third sensor data 108(3), the server(s) 110 may determine a difference between one or more physiological values indicated by the second sensor data 108(2) and one or more physiological values indicated by the third sensor data 108(3). Information indicative of the difference may be included in output data 114(2) provided to the user device 112. For example, after completion of an activity, an output 102 that indicates a reduction in a blood pressure associated with the user 104 may be presented. In some implementations, the output 102 may include an interface requesting additional information from the user 104. In other implementations, the output data 114(2) may indicate particular times during performance of the activity or particular actions by the user 104. For example, if a posture or the position of one or more body parts of the user 104 was suboptimal during performance of the activity, an output 102 that includes corrective instruction or an indication of the posture or position may be presented.

In some implementations, the effectiveness of particular activities may be used at a future time to determine output 102 that is presented to the user 104. For example, if a first type of activity successfully changes the physiological state of the user 104 while a second type of activity does not successfully change the physiological state, at a future time, output 102 associated with the first type of activity may be presented to the user 104. In some cases, output 102 that is determined to be effective for a particular user 104 may be presented to other demographically similar users 104, while output 102 that is ineffective for the particular user 104 may not be presented.

While FIG. 4 depicts output data 114(2) that indicates a relationship between physiological values of the second sensor data 108(2) and the third sensor data 108(3), in other implementations, the output data 114(2) may indicate a relationship between the first sensor data 108(1) and third sensor data 108(3). For example, the output data 114(2) may be used to generate an output 102 that compares sensor data 108(1) acquired before the user 104 initiated the activity to sensor data 108(3) acquired after the user completed the activity.

Figure 5:
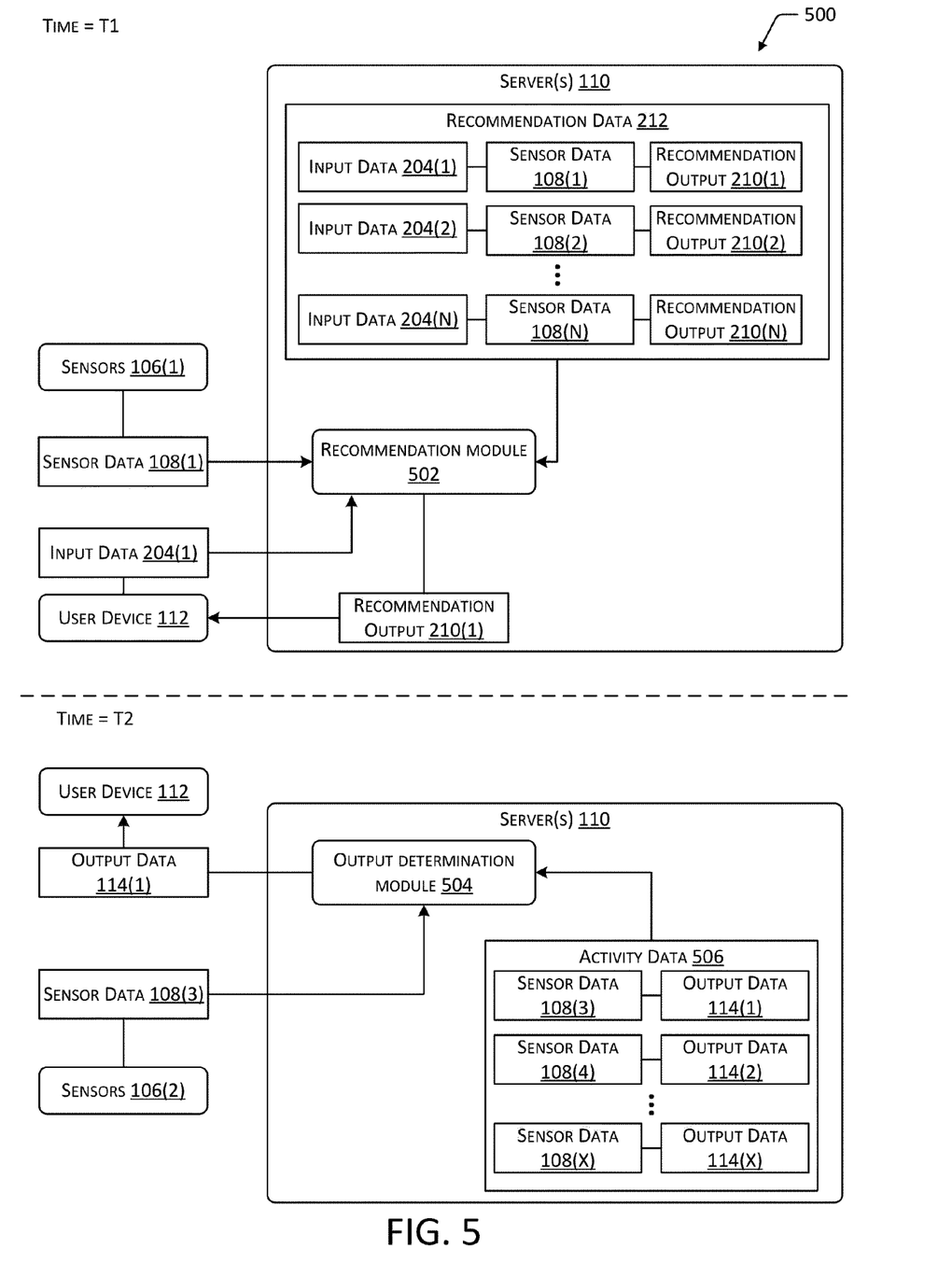
FIG. 5 depicts an implementation of a system that may determine recommendation output and other output data based on data received from sensors and user devices.

FIG. 5 depicts an implementation of a system 500 that may determine recommendation output 210 and other output data 114 based on data received from sensors 106 and user devices 112. While FIG. 5 depicts the system 500 including one or more servers 110 that receive data from sensors 106 and user devices 112 and provide data to user devices 112, in other implementations, one or more of the functions described with regard to the server(s) 110 may be performed by a user device 112 or by a sensor 106.

At a first time T1, a recommendation module 502 associated with the server(s) 110 may receive input data 204(1) from a user device 112 and sensor data 108(1) from one or more sensors 106(1). For example, a user 104 may provide input to a user device 112 or to another computing device using one or more input devices, such as a touchscreen, keyboard, mouse device, microphone, and so forth. In some implementations, a user interface may be presented to solicit input data 204 from the user 104. For example, a user interface may present questions or prompts for particular information, such as an age of the user 104 or a number of hours the user 104 slept during the previous night. In some implementations, the recommendation module 502 may access preexisting user data in place of or in addition to the input data 204(1). For example, based on the user device 112 or a user account associated with the user device 112, an identity of the user 104 may be determined, and existing user data associated with the user 104 may indicate one or more characteristics of the user 104. The sensor data 108(1) may include physiological values determined from one or more sensors 106(1) worn or held by the user 104, image data from one or more cameras, audio data from one or more microphones, and so forth. For example, a body position, facial expression, or tone or pace of speech uttered by the user 104 may be included in the sensor data 108(1) in addition to or in place of physiological values such as a heart rate, respiration rate, blood pressure, and so forth.

The recommendation module 502 may determine correspondence between the received input data 204(1) and sensor data 108(1) and recommendation data 212. The recommendation data 212 may associate particular recommendation output 210 with corresponding input data 204 and sensor data 108. In some cases, a particular recommendation output 210 may be associated with a particular characteristic or set of characteristics that may be determined based on input data 204. In other cases, a particular recommendation output 210 may be associated with a particular physiological value or set of physiological values determined based on sensor data 108. Additionally, a particular recommendation output 210 may be associated with a combination of characteristics and physiological values that may be determined from both input data 204 and sensor data 108. By way of example, FIG. 5 depicts the recommendation data 212 associating a first recommendation output 210(1) with first input data 204(1) and first sensor data 108(1), and a second recommendation output 210(1) with second input data 204(2) and second sensor data 208(2). Any number of recommendation outputs 210(N) may be associated with any number of corresponding input data 204(N) and sensor data 108(N). Additionally, while FIG. 5 depicts each recommendation output 210 associated with a single input data 204 and sensor data 108, in other implementations, a recommendation output 210 may be associated with multiple input data 204 or multiple sensor data 108.

FIG. 5 depicts the recommendation module 502 receiving first sensor data 108(1) from sensors 106(1), and first input data 204(1) from a user device 112. Based on the recommendation data 212 that associates a first recommendation output 210(1) with the first input data 204(1) and first sensor data 108(1), the first recommendation output 210(1) may be provided to the user device 112.

At a second time T2, an output determination module 504 associated with the server(s) 110 may receive sensor data 108(3) from one or more sensors 106(2) and provide output data 114(1) to the user device 112 or another computing device based on the received sensor data 108(3). For example, after a user 104 initiates an activity, such as the activity initiated in the recommendation output 210(1), sensor data 108 associated with the user 104 may be used to determine output data 114 that is provided to the user device 112. In some implementations, the sensor data 108(3) received by the output determination module 504 may be received from the same sensors 106(1) that provide sensor data 108(1) to the recommendation module 502. In other implementations, the sensor data 108(3) may be received from one or more different sensors 106(2). For example, prior to performance of an activity, a user 104 may interact with a first set of sensors 106(1), while during performance of the activity, the user 104 may interact with a second set of sensors 106(2).

The output determination module 504 may determine correspondence between the sensor data 108(3) and activity data 506. The activity data 506 may associate sensor data 108 with corresponding output data 114. For example, particular output data 114 may be associated with a particular physiological value or set of physiological values that may be determined based on sensor data 108. Continuing the example, FIG. 5 depicts the activity data 506 associating first output data 114(1) with third sensor data 108(3) and second output data 114(2) with fourth sensor data 108(4). Any number of output data 114(X) may be associated with any number of corresponding sensor data 108(X). Additionally, while FIG. 5 depicts each output data 114 associated with a single sensor data 108, in other implementations, an output data 114 may be associated with multiple sensor data 108.

FIG. 5 depicts the output determination module 504 receiving third sensor data 108(3) from sensors 106(2). Based on the activity data 506 that associates first output data 114(1) with the third sensor data 108(3), the first output data 114(1) may be provided to the user device 112.

Figure 6:
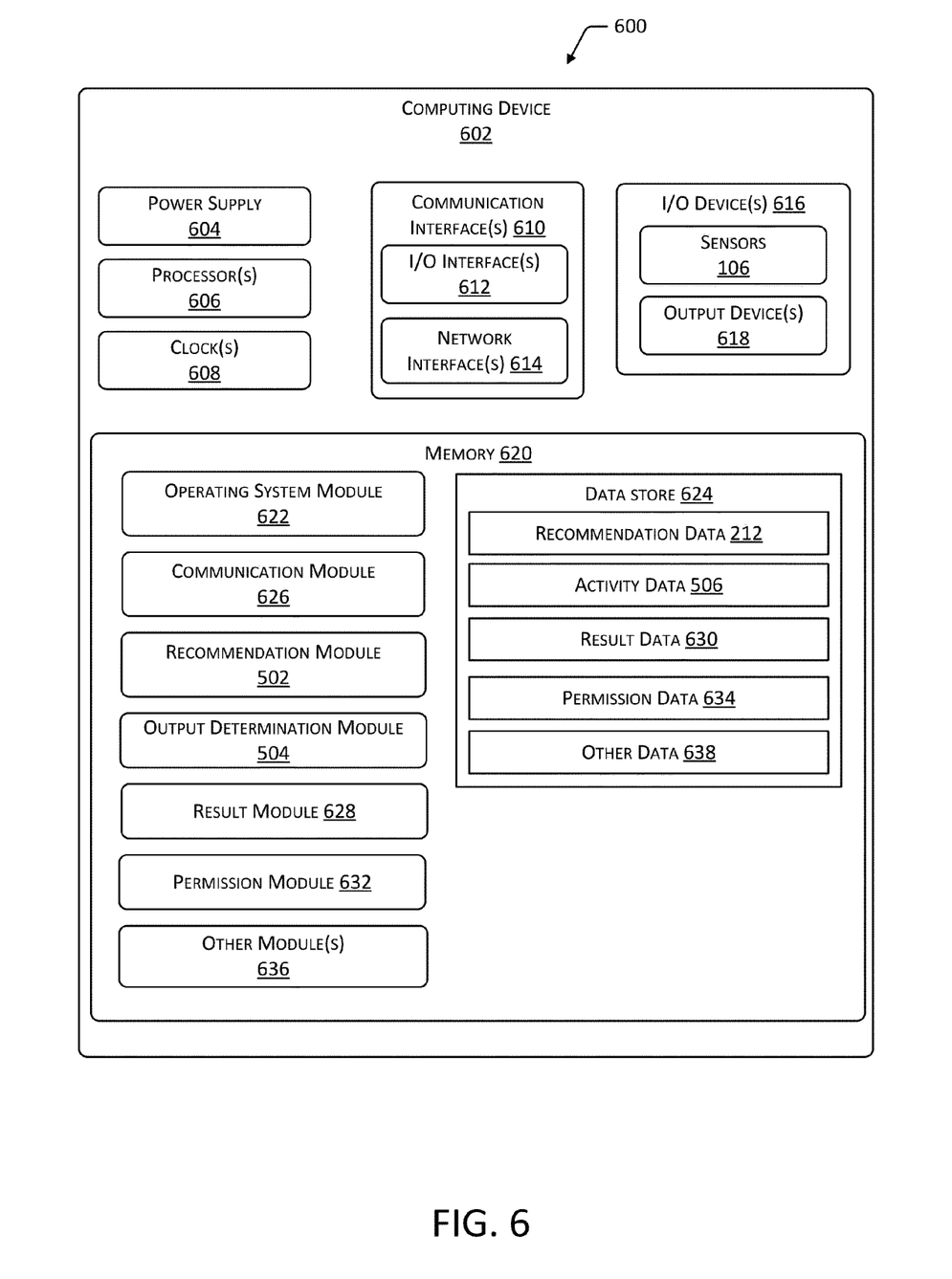
FIG. 6 is a block diagram illustrating an implementation of a computing device within the present disclosure.

FIG. 6 is a block diagram 600 illustrating an implementation of a computing device 602 within the present disclosure. The computing device 602 may include a server 110, a user device 112, a computing device 602 incorporating one or more sensors 106, or any combination of these devices. Additionally, while FIG. 6 depicts a single block diagram 600 of a computing device 602, any number and any type of computing devices 602 may be used to perform the functions described herein. For example, one or more servers 110, user devices 112, or computing devices 602 that include or communicate with sensors 106 may be used in combination to determine recommendation output 210 and output data 114 based on received input data 204 and sensor data 108. For example, a single computing device 602 that includes one or more sensors 106, such as a wearable computing device 602, may receive user input, acquire sensor data 108 using the sensor(s) 106, provide sensor data 108 to a server 110 or other computing device 602, receive output data 114, and present output 102 based on the output data 114. In other implementations, a computing device 602 that includes sensors 106 or a user device 112 may be used to determine output data 114 without communicating with a server 110 or other computing device 602 outside of the environment associated with the user 104.

One or more power supplies 604 may be configured to provide electrical power suitable for operating the components of the computing device 602. In some implementations, the power supply 604 may include a rechargeable battery, fuel cell, photovoltaic cell, power conditioning circuitry, and so forth.

The computing device 602 may include one or more hardware processor(s) 606 (processors) configured to execute one or more stored instructions. The processor(s) 606 may include one or more cores. One or more clock(s) 608 may provide information indicative of date, time, ticks, and so forth. For example, the processor(s) 606 may use data from the clock 608 to generate a timestamp, trigger a preprogrammed action, and so forth.

The computing device 602 may include one or more communication interfaces 610, such as input/output (I/O) interfaces 612, network interfaces 614, and so forth. The communication interfaces 610 may enable the computing device 602, or components of the computing device 602, to communicate with other computing devices 602 or components of the other computing devices 602. The I/O interfaces 612 may include interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 612 may couple to one or more I/O devices 616. The I/O devices 616 may include any manner of input devices or output devices associated with the computing device 602. For example, I/O devices 616 may include touch sensors, displays, touch sensors integrated with displays (e.g., touchscreen displays), keyboards, mouse devices, microphones, image sensors, cameras, scanners, speakers, haptic devices, printers, and so forth. In some implementations, the I/O devices 616 may be physically incorporated with the computing device 602. In other implementations, I/O devices 616 may be externally placed.

The I/O devices 616 may also include one or more sensors 106, that may be in direct or wireless communication with the computing device 602. Various types of sensors 106 may be used, and sensors 106 may be associated with various objects including the computing device 602, an object worn by a user 104, an object within an environment with the computing device 602 or user 104, and so forth. For example, sensors 106 may include a blood pressure sensor, a heart rate monitor, pressure sensors or touch sensors for determining a position of one or more body parts of a user 104, a microphone for receiving audio data indicative of user breathing or speech, or ambient noise, a temperature sensor, an accelerometer, magnetometer, location sensor, proximity sensor, or other component for detecting motion, orientation, or location of the user 104. The computing device 602 or environment associated with the user 104 may also include one or more output devices 618, such as haptic output devices, speakers or other audio output devices, display devices, scent dispensers, lights, devices configured to modify an ambient temperature or humidity, and so forth.

The network interfaces 614 may be configured to provide communications between the computing device 602 and other devices, such as the I/O devices 616, routers, access points, and so forth. The network interfaces 614 may include devices configured to couple to one or more networks including local area networks (LANs), wireless LANs (WLANs), wide area networks (WANs), wireless WANs, and so forth. For example, the network interfaces 614 may include devices compatible with Ethernet, Wi-Fi, Bluetooth, ZigBee, Z-Wave, 3G, 4G, 5G, LTE, and so forth.

The computing device 602 may include one or more busses or other internal communications hardware or software that allows for the transfer of data between the various modules and components of the computing device 602.

As shown in FIG. 6, the computing device 602 may include one or more memories 620. The memory 620 may include one or more computer-readable storage media (CRSM). The CRSM may be any one or more of an electronic storage medium, a magnetic storage medium, an optical storage medium, a quantum storage medium, a mechanical computer storage medium, and so forth. The memory 620 may provide storage of computer-readable instructions, data structures, program modules, and other data for the operation of the computing device 602. A few example modules are shown stored in the memory 620, although the same functionality may alternatively be implemented in hardware, firmware, or as a system on a chip (SoC).

The memory 620 may include one or more operating system (OS) modules 622. The OS module 622 may be configured to manage hardware resource devices such as the I/O interfaces 612, the network interfaces 614, the I/O devices 616, and to provide various services to applications or modules executing on the processors 606. The OS module 622 may implement a variant of the FreeBSD operating system as promulgated by the FreeBSD Project; UNIX or a UNIX-like operating system; a variation of the Linux operating system as promulgated by Linus Torvalds; the Windows operating system from Microsoft Corporation of Redmond, Washington, USA; or other operating systems.

One or more data stores 624 and one or more of the following modules may also be associated with the memory 620. The modules may be executed as foreground applications, background tasks, daemons, and so forth. The data store(s) 624 may use a flat file, database, linked list, tree, executable code, script, or other data structure to store information. In some implementations, the data store(s) 624 or a portion of the data store(s) 624 may be distributed across one or more other devices including other computing devices 602, network attached storage devices, and so forth.

A communication module 626 may be configured to establish communications with one or more other computing devices 602. Communications may be authenticated, encrypted, and so forth.

The memory 620 may also store the recommendation module 502. The recommendation module 502 may determine a recommendation output 210 that may be provided based on recommendation data 212. The recommendation data 212 may associate one or more of input data 204 or sensor data 108 with a recommendation output 210. For example, each recommendation output 210 may be associated with one or more physiological values or user characteristics, and based on input data 204 or sensor data 108 received by the computing device 602, a corresponding recommendation output 210 may be provided for presentation. In some implementations, the recommendation module 502 may access existing user data associated with a user device 112, user account, or user 104. For example, the user data may indicate one or more characteristics or physiological values that may correspond to one or more of the recommendation outputs 210. In such a case, existing user data may be used in addition to or in place of input data 204 or sensor data 108.

The memory 620 may additionally store the output determination module 504. The output determination module 504 may determine output data 114 that may be provided based on activity data 506. The activity data 506 may associate sensor data 108 with output data 114. For example, each output data 114 may be associated with a particular physiological value or set of physiological values. Continuing the example, the output data 114 may associate threshold values or threshold ranges for a physiological value with a corresponding output data 114. If sensor data 108 indicating a physiological value within a threshold range is received, the corresponding output data 114 may be provided for presentation. In cases where received sensor data 108 does not correspond to output data 114 indicated in the activity data 506, default output data 114 may be provided for presentation.

The memory 620 may also include a result module 628. The result module 628 may generate an output 102 indicative of a difference between physiological values determined from sensor data 108, a result of performance of an activity, and so forth. For example, as described with regard to FIG. 4, output data 114 may be generated that indicates a relationship between physiological values determined at different times, such as before an activity is initiated, during performance of the activity, and after completion of the activity. The result module 628 may determine a difference or other type of relationship between physiological values and generate output data 114 indicative of a relationship between the physiological values. In some implementations, the result module 628 may access result data 630, which may indicate one or more rules, algorithms, or other methods for comparing different physiological values determined at different times.

The memory 620 may include a permission module 632. The permission module 632 may be used to acquire permission from users 104 to collect sensor data 108, input data 204, and so forth. For example, a user 104 may be provided with a prompt or other type of user interface that enables the user 104 to consent or opt-in, allowing for the acquisition and use of sensor data 108 associated with the user 104. The permission module 632 or another module may encrypt, anonymize, or de-identify, or otherwise modify the received sensor data 108 and input data 204, such as to increase the security and privacy of the data. Permission data 634 may be maintained, which may indicate users 104 that have opted to permit use of sensor data 108, users 104 that have declined to provide such permission, a record of the transmissions of sensor data 108 and input data 204, and so forth. For example, if a user 104 does not provide authorization for collection of certain types of sensor data 108, use of certain types of sensors 106, such as cameras or sensors 106 that determine particular physiological values may be prevented. In some cases, a user 104 may authorize use of particular types of sensor data 108 for determination of output data 114 to be provided to a server 110, but may decline to permit use of the sensor data 108 to identify the user 104 or to be provided to other parties.

Other modules 636 may also be present in the memory 620. For example, user interface modules may be used to generate a user interface for presentation of output 102 and determine characteristics of the user interface. Other modules 636 may also include encryption modules to encrypt and decrypt communications between computing devices 602, authentication modules to authenticate communications sent or received by computing devices 602, administrative modules to assign, determine, and manage user permissions to access or modify data associated with computing devices 602, and so forth.

Other data 638 within the data store(s) 622 may include configurations, settings, preferences, and default values associated with computing devices 602. Other data 638 may also include encryption keys and schema, access credentials, and so forth. Other data 638 may include user interface data for generation of user interfaces presented on a user device 112. Other data 638 may also include network data indicative of networks accessible to one or more computing devices 602.

In different implementations, different computing devices 602 may have different capabilities or capacities. For example, servers 110 may have greater processing capabilities or data storage capacity than user devices 112.

The processes discussed in this disclosure may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described in this disclosure. The computer-readable storage medium may be one or more of an electronic storage medium, a magnetic storage medium, an optical storage medium, a quantum storage medium, and so forth. For example, the computer-readable storage media may include, but is not limited to, hard drives, floppy diskettes, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A system comprising:
an input device;
a photoplethysmograph (PPG);
an output device;
one or more memories storing computer-executable instructions; and
one or more hardware processors to execute the computer-executable instructions to:
acquire, using the input device, first input data indicating a characteristic of a user;
determine, using data from the PPG, a first respiration rate of the user;
determine, based on the characteristic and the first respiration rate, a recommendation that indicates a first output, wherein the first output is associated with a first type of activity and a length of time to perform the first type of activity;
present, using the output device, the recommendation;
acquire, using the input device, second input data indicating acceptance of the recommendation;
present, using the output device, the first output associated with the first type of activity;
determine, using data from the PPG during presentation of the first output, a second respiration rate of the user;
determine a threshold range between a first threshold value and a second threshold value based on activity data that associates the threshold range with the first type of activity and with a second output;

determine that the second respiration rate is between the first threshold value and the second threshold value; and based on the second respiration rate being between the first threshold value and the second threshold value, present, using the output device, the second output.

2. The system of claim 1, further comprising:
a camera; and
computer-executable instructions to:
acquire, using the camera during presentation of the first output, image data indicative of a first position of at least a portion of a body of the user;
determine correspondence between the first position and a reference position; and
include an indication of a relationship between the first position and the reference position in the second output.

3. The system of claim 1, further comprising computer-executable instructions to:
determine calendar data associated with the user, wherein the calendar data indicates one or more available times for performance of the first type of activity;
determine a first time of the one or more available times for performance of the activity based at least in part on the calendar data and the length of time for the first type of activity;
include the first time in the first output; and
in response to the second input data, add an indication of the first type of activity to the calendar data.

4. A method comprising:
providing, at a first time, first output data to an output device, wherein the first output data is associated with performance of an activity;
determining one or more first threshold values based on activity data that associates the activity with the one or more first threshold values;
acquiring first sensor data from one or more sensors associated with a user, wherein the first sensor data indicates motion of the user that is less than a second threshold value;
in response to the first sensor data, acquiring second sensor data from the one or more sensors, wherein the second sensor data indicates one or more first physiological values;
determining a relationship between a first physiological value of the one or more first physiological values and the one or more first threshold values;
determining second output data that is associated with the relationship between the first physiological value and the one or more first threshold values; and
providing, at a second time after the first time, the second output data to the output device.

5. The method of claim 4, wherein the one or more first physiological values include one or more of: heart rate, blood pressure, respiration rate, oxygen saturation value, temperature, blood perfusion index, or heart rate variability.

6. The method of claim 4, wherein the first output data is associated with performance of a first portion of the activity and the second output data is associated with performance of a second portion of the activity, the method further comprising:
acquiring, at a third time before the first time, one or more historical values for the first physiological value of the one or more first physiological values, wherein the one or more first threshold values are further determined based on the one or more historical values, and wherein the one or more first threshold values further include a third threshold value and a fourth threshold value for the first physiological value; and determining, at a fourth time after the first time and before the second time, that the first physiological value of the one or more first physiological values is between the third threshold value and the fourth threshold value;
wherein the second output data is provided to the output device in response to the first physiological value being between the third threshold value and the fourth threshold value.

7. The method of claim 4, wherein the first output data is associated with performance of a first portion of the activity, and wherein the one or more first threshold values include a threshold minimum value and a threshold maximum value, the method further comprising:
determining, at a third time after the first time and before the second time, that the first physiological value of the one or more first physiological values is one or more of: less than the threshold minimum value or greater than the threshold maximum value;
wherein the second output data is provided to the output device in response to the first physiological value, and the second output data includes one or more of: an indication of the first physiological value or an instructional prompt.

8. The method of claim 4, further comprising:
acquiring, at a third time after the first time and before the second time, audio data using a microphone; and
determining, based on the audio data, one or more of a volume of sound or a type of sound represented by the audio data;
wherein the second output data is further determined based at least in part on the one or more of the volume of sound or the type of sound.

9. The method of claim 4, further comprising:
acquiring, at a third time after the first time and before the second time, image data using a camera; and
determining, based on the image data, a first position of at least a portion of a body of the user; and
determining correspondence between the first position and a reference position;
wherein the second output data is further determined based at least in part on a relationship between the first position and the reference position.

10. The method of claim 4, further comprising:
acquiring, at a third time after the first time and before the second time, image data using a camera; and
determining, based on the image data, one or more of a facial expression or body position associated with the user;
wherein the second output data is further determined based at least in part on the one or more of the facial expression or the body position.

11. The method of claim 4, further comprising:
at a third time before the first time, acquiring one or more of:
third sensor data from the one or more sensors, wherein the third sensor data indicates one or more second physiological values; or
first input data from an input device, wherein the first input data indicates a first characteristic of the user;
determining that the first output data is associated with one or more of:
at least one second physiological value of the one or more second physiological values; or
the first characteristic of the user;
providing a recommendation indicative of the first output data to the output device; and
receiving input indicating acceptance of the recommendation, wherein the first output data is provided to the output device in response to the input.

12. The method of claim 11, further comprising:
at a fourth time subsequent to completion of the activity, acquiring one or more of:
fourth sensor data from the one or more sensors, wherein the fourth sensor data indicates one or more third physiological values; or
second input data from the input device, wherein the second input data indicates a second characteristic of the user; and
providing third output data to the output device, wherein the third output data indicates one or more of:
a relationship between a third physiological value of the one or more third physiological values and the at least one second physiological value of the one or more second physiological values; or
a relationship between the second characteristic and the first characteristic.

13. A system comprising:
one or more memories storing computer-executable instructions; and
one or more hardware processors to execute the computer-executable instructions to:
at a first time, determine one or more of:
user data indicative of a first characteristic of a user; or
first sensor data indicative of one or more first physiological values associated with the user;
determine, based on one or more of the first characteristic or a first physiological value of the one or more first physiological values, a recommendation indicative of first output data, wherein the first output data is associated with performance of a type of activity for a length of time;
provide the first output data to an output device;
at a second time after the first time, acquire second sensor data indicative of one or more second physiological values associated with the user; and
provide second output data to the output device, wherein the second output data corresponds to one or more of:
the one or more second physiological values;
a relationship between the first physiological value and a second physiological value of the one or more second physiological values; or
a relationship between the first characteristic and the second physiological value.

14. The system of claim 13, further comprising computer-executable instructions to:
acquire audio data indicative of user speech from a microphone associated with the user;
determine, based on the audio data, an emotional state associated with the user speech; and
wherein one or more of the first output data or the second output data is further associated with the emotional state.

15. The system of claim 13, further comprising computer-executable instructions to:
acquire audio data from a microphone; and
determine, based on the audio data, one or more of a volume of sound or a type of sound represented by the audio data;
wherein the first output data is further associated with the one or more of the volume of sound or the type of sound and includes an indication regarding the one or more of the volume of sound or the type of sound.

16. The system of claim 13, further comprising computer-executable instructions to:
at a third time after the first time and before the second time, determine third output data based on the one or more second physiological values; and
provide the third output data to the output device, wherein the third output data includes an instruction to perform an action to modify a second physiological value of the one or more second physiological values.

17. The system of claim 13, further comprising computer-executable instructions to:
determine calendar data associated with the user, wherein the calendar data indicates one or more available times for performance of the type of activity;
determine a first time of the one or more available times for performance of the type of activity based at least in part on the calendar data and the length of time for the type of activity; and
include the first time in the recommendation.

18. The system of claim 13, further comprising computer-executable instructions to:
acquire, using a camera, image data indicative of one or more of a facial expression of the user or a position of at least a portion of a body of the user;
wherein the first output data is further associated with the one or more of the facial expression or the position.

19. The system of claim 13, further comprising computer-executable instructions to:
acquire, using a camera, image data indicative of motion of the user; and
determine that the motion of the user is less than a threshold value;
wherein one or more of the first output data or the second output data is further provided in response to the motion being less than the threshold value.

20. The system of claim 13, further comprising computer-executable instructions to:
acquire, using one or more sensors associated with the user, third sensor data indicative of motion of the user; and
determine that the motion of the user is less than a threshold value;
wherein one or more of the first output data or the second output data is further provided in response to the motion being less than the threshold value.

* * * * *